United States Patent [19]
Pitner

[11] Patent Number: 5,837,695
[45] Date of Patent: Nov. 17, 1998

[54] FLUORESCENT CHLAMYDIA ANTIGEN SUBSTRATE

[75] Inventor: J. Bruce Pitner, Durham, N.C.

[73] Assignee: Becton Dickinson and Company, Franklin Lakes, N.J.

[21] Appl. No.: 701,340

[22] Filed: Aug. 22, 1996

[51] Int. Cl.$^6$ .......................... C07H 15/24; A61K 31/70
[52] U.S. Cl. ................... 514/61; 514/23; 514/25; 536/17.1; 536/17.2; 536/18.1; 536/18.7; 536/54
[58] Field of Search ...................................... 536/18.1, 4.1, 536/17.1, 17.2, 18.7, 54; 514/25, 23, 61

[56] References Cited

U.S. PATENT DOCUMENTS 5,085,986   2/1992   Mauck et al. .......................... 435/7.36

*Primary Examiner*—Elli Peselev
*Attorney, Agent, or Firm*—David W. Highet, Esq.

[57] ABSTRACT

The present invention relates to a unique fluorescently labeled Chlamydial antigen. This fluorescently labeled Chlamydial antigen is useful in immunoassay-type formatted systems for the detection of antibodies to Chlamydia or unlabeled Chlamydia antigens.

3 Claims, 6 Drawing Sheets

Fluorescent Substrate

R' or R" = H, and
R' or R" = [acetyl group structure]

(Probably a mixture of these two isomers)

FIG-4 Chlamydia Fluorescent Substrate: MAb Assays

FIG-5 FP Competition Assay for Chlamydia LPS

FLUORESCENT CHLAMYDIA ANTIGEN SUBSTRATE

BACKGROUND OF THE INVENTION

The present invention relates broadly to the field of immunodiagnostics. More particularly, the present invention relates to compounds which are useful in immunoassays to diagnose Chlamydial infections. The compounds are also useful in screening assays to identify Chlamydia antigen ligands which are also useful in assays to diagnose Chlamydial infection.

Chlamydia are Gram negative obligate intracellular organisms which are known to be responsible for trachoma, inclusion conjunctivitis and lymphogranuloma verereum. Chlamydia is also believed to be the causitive organism of nonspecific urethritis, proctitis, urethral stricture, acute epididymitis, hypertrophic erosion of the cervix, purulent cervical mucus and salpingitis.

Specimens from which Chlamydial organisms may be recovered include conjunctival swabs, endourethral swabs, endocervical swabs, Fallopian tube biopsies, epididymal aspirates, lymph node aspirates, and for infant respiratory infections, nasopharyngeal swabs and tracheobronchial aspirates. Identification of Chlamydial organisms in specimens or tissue culture involves demonstration of characteristic intracytoplasmic inclusions by use of Giemsa stain, iodine stain, other stains or fluorescent antibody technique.

Fluorescent antibody techniques are presently believed to be more sensitive and specific than staining techniques for initial detection of clinical isolates. Such fluorescent antibody techniques are practiced as generally taught in Stamm, W. E. et al., *J. Clin. Microbiol.* 17, 666–668 (1983) and Thomas, B. J. et al., *J. Clin. Microbiol.* 6, 285–292 (1977). Briefly, these techniques utilize an antibody sandwich assay format wherein one of the antibodies is fluorescently labeled, and detection of fluorescence intensity values indicates the presence of Chlamydia antigen in a sample.

Another fluorescent antibody technique is taught in PCT Publication No. WO 86/02355. This is a fluorescence polarization assay conducted with a fluorescently labeled antibody to Chlamydia antigen.

One of the significant drawbacks of Chlamydia assays which utilize fluorescently labeled antibody is the inability to conduct homogenous assays. These conventional assays with labeled antibody require a separation of bound antibody from un-bound antibody in order to detect presence or absence of Chlamydia antigen in a sample. Such separation is usually accomplished with at least one wash step or by chromatographic methods.

SUMMARY OF THE INVENTION

Figure 1:
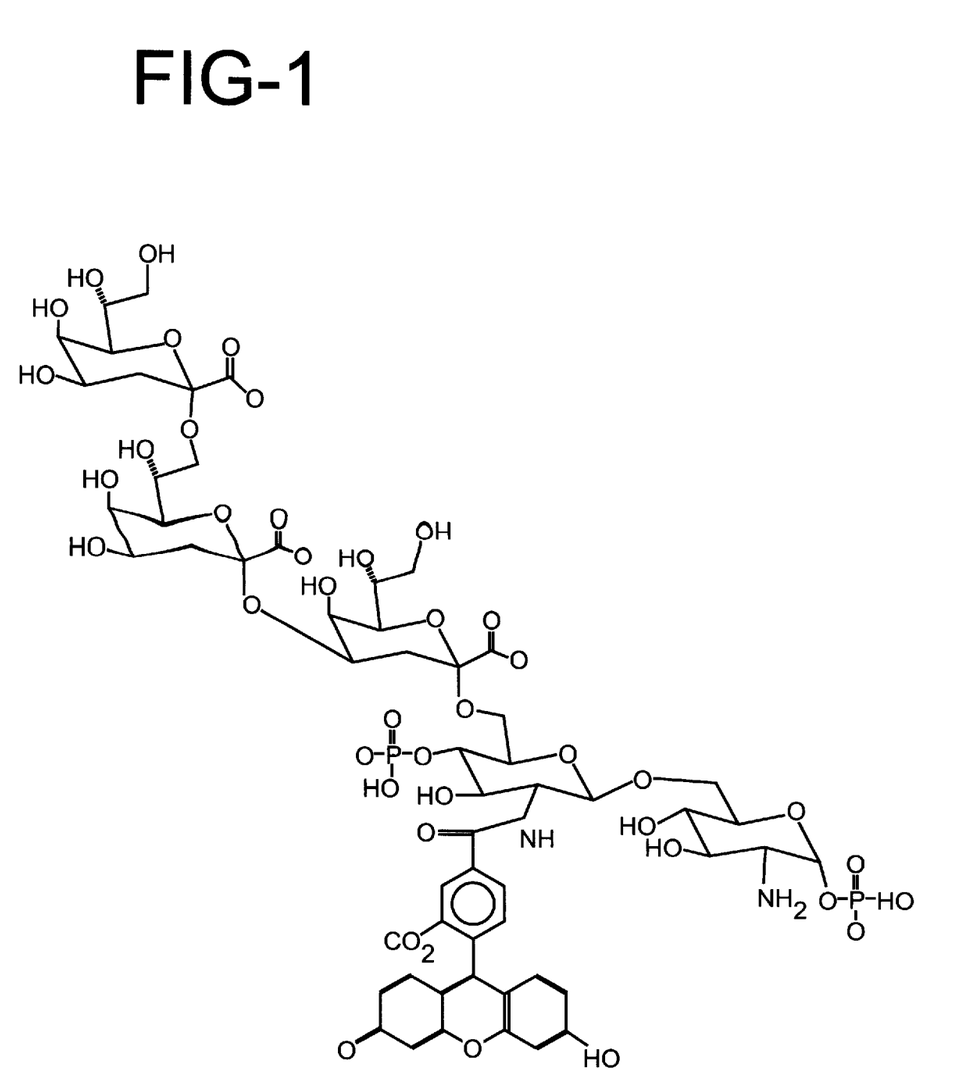
FIG. 1 shows the structural formula of one isomer of the present invention.
Figure 2:
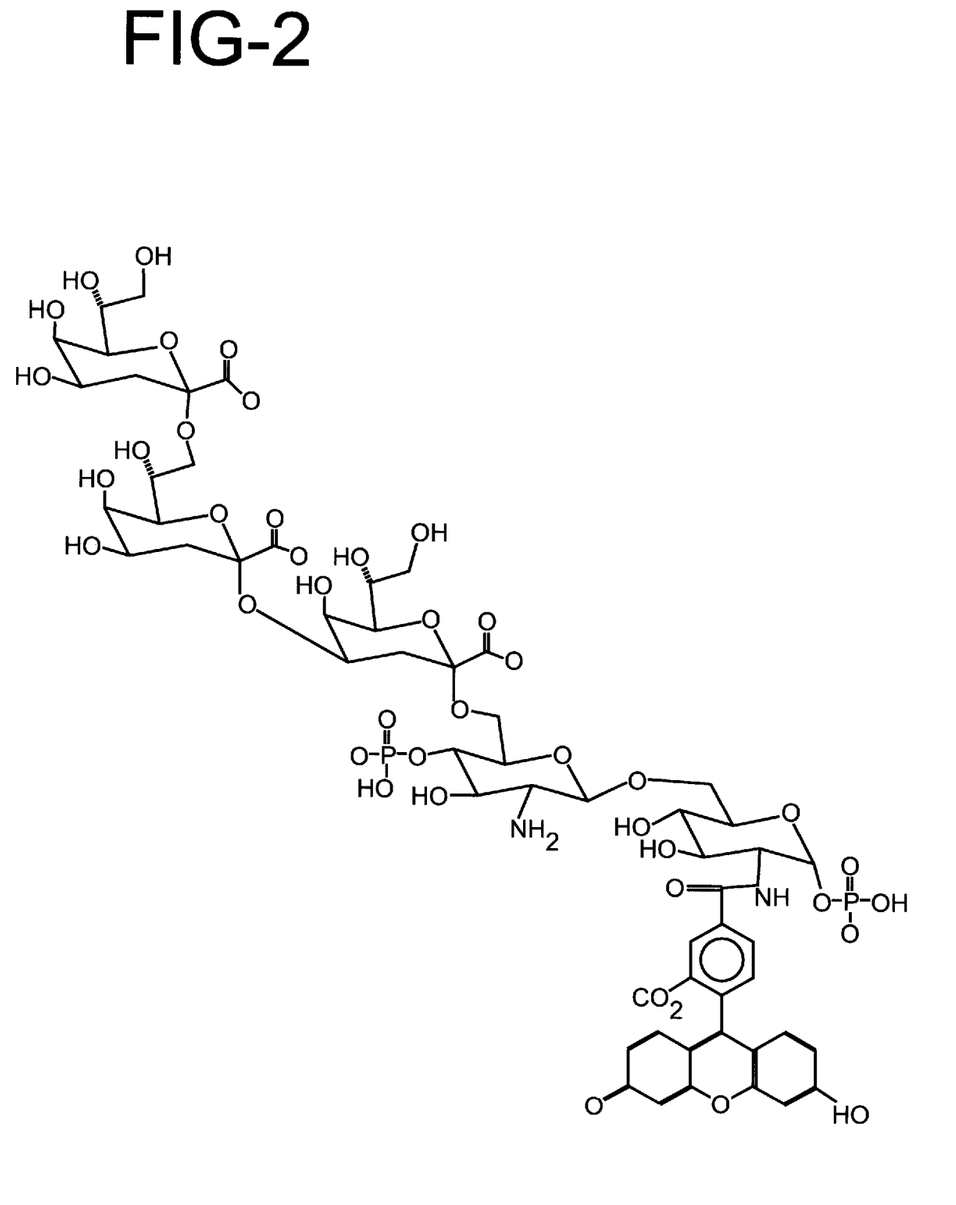
FIG. 2 shows the structural formula of another isomer of the present invention.

The present invention permits a direct detection of Chlamydia antigen without wash step or application of chromatographic methods by providing a compound of the formula of FIG. 1 wherein R is —OH or —OPO$_3$H$_2$ and R$^1$ is —OH or or a compound of the formula of FIG. 2 wherein R is —OH or —OPO$_3$H$_2$.

These compounds or a composition including both compounds may be used as part of an ligand/antigen complex in competition based assays wherein the presence of Chlamydia antigen in a sample is indicated by a detectable change in a fluorescence value such as a fluorescence polarization value, a fluorescence anisotropy value or a fluorescence intensity value. The compounds are also useful in assays for the direct detection of ligands such as Chlamydia antibodies in a sample as well as in screening assays to identify ligands which specifically bind to Chlamydia antigen.

BRIEF DESCRIPTION OF THE DRAWINGS

The various objects, advantages and novel features of the invention will be more readily appreciated from the following detailed description when read in conjunction with the appended figures in which.

DETAILED DESCRIPTION OF THE INVENTION

As stated above, the present invention relates to compounds of the formulas of FIG. 1 and FIG. 2.

Figure 3:
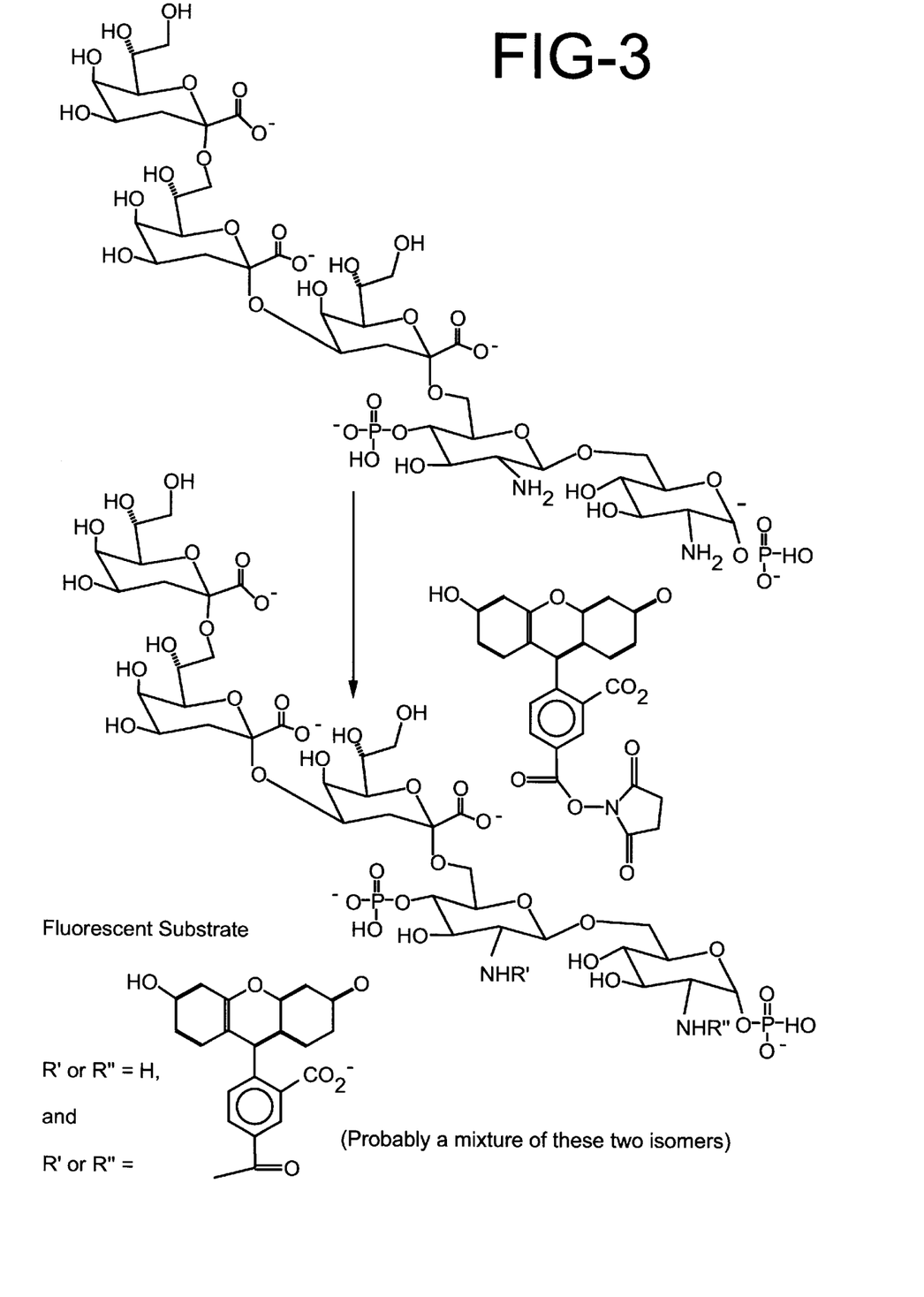
FIG. 3 is a schematic diagram of a reaction used to make fluorescently labeled Chlamydia substrate of the present invention.

Although described more specifically in the Examples, the compounds of the present invention are made by reacting de-lipified Chlamydia pentasaccharide antigen with a fluorescent dye in a manner to yield site specific attachment of the dye to amino groups of the Chlamydia antigen. Such attachment provides a 1 to 1 ratio of fluorophore to antigen, and does not interfere with the more immunogenic tri KDO portion of the antigen. The a reaction is set forth schematically in FIG. 3, wherein a slightly greater than 1:1 ratio of dye to antigen is used. Such a reaction produces a composition which is a mixture of the two compounds (isomers) of FIG. 1 and FIG. 2.

The de-lipified Chlamydia pentasaccharide was obtained from Dr. Helmut Brade of the Forschunginstitut Borstel, Borstel, Germany. The lipopentasaccharide is produced using the recombinant *E. coli* strain F515-207 as described by Holst et al, *Eur. J. Biochem.* 214: 703–710 (1993) to obtain a Chlamydia cell wall lipopolysaccharide (LPS) common to all three species of Chlamydia—*C. trachomatis, C. pneumoniae* and *C. psittaci*. After purification, Chlamydia LPS is selectively de-lipified to obtain the core pentasaccharide bisphosphate (PSBP):

á-Kdo-(2-8)-á

In general, a direct assay involves the determination of a fluorescence value for the fluorescently labeled Chlamydia antigen of the present invention followed by exposure of the fluorescently labeled Chlamydia antigen to a sample which may or may not contain a ligand such as an antibody which specifically binds the antigen. A second value is then determined for the sample exposed to fluorescently labeled Chlamydia antigen. A change in the fluorescence value indicates the presence of a ligand which is bound to the fluorescently labeled Chlamydia antigen, thus causing the change of value. Conversely, an unchanged value indicates the absence of such a ligand in the sample.

Direct assays such as those just described above are generally used to diagnose disease conditions or exposure to a causative agent of a disease. The direct assays may also be used to identify and screen for ligands such as antibodies which may then be used in diagnostic or therapeutic processes.

The following examples illustrate specific embodiments of the present invention. As would be apparent to skilled artisans, various changes and modifications are possible and are contemplated within the scope of the invention described.

EXAMPLE 1

Preparation of Fluorescently Labeled Chlamydia Antigen

Purified Chlamydia pentasaccharide bisphosphate (PSBP), á-Kdo-(2-8)-á-Kdo-(2-4)-á-Kdo-(2-6)-â-GLcN-4P-(1-6)-á-GlcN-1P was obtained from the recombinant *E. coli* strain F515-207 as described Holst et al, *Eur. J. Biochem.* 214:703–710 (1993). A 50 uL (1 mg) aliquot of a 20 mg/ml solution of PBSP in $H_2O$ was added to 100 uL of $NaHCO_3$ buffer. To this solution, 0.5 mg (1.3 equivalents) of fluorescein 5-carboxy N-hydroxysuccinimde (Molecular Probes, Eugene, Oreg.) in 5 uL DMSO was added. This solution was kept in the dark at room temperature for 2 days.

After being stored for 3 days at 4° C., the solution was passed over a NAP-5 column (Pharmacaia) and eluted with PBS buffer. The second through ninth fractions with volumes between 0.5 and 1.0 mL had fluorescein present and were assayed. This was done by dilution of an aliquot of each fraction to an apparent fluorophore concentration of 1–2 nM in 1.0 mL of PBS buffer and taking initial fluorescence polarization (FP) values at ambient temperature, followed by readings taken 15 minutes after the addition of monoclonal antibody S25-23 (Dr. Helmut Brade, Forschunginstitut Borstel, Borstel, Germany) (either 10 or 20 uL of a 1.36 mg/mL solution) to each aliquot. The second and third fractions appeared to contain fluorescent substrate because of the high initial FP and the further increases in FP they demonstrated with the antibody. Subsequent fractions appeared to contain unreacted fluorescein NHS ester or related reaction byproducts. The third fraction was used in all subsequent fluorescence binding assays described in the Examples below. Analysis of the fractions from the substrate preparation is set forth below:

Fluorescence Polarization of Substrate Fractions (in mP) plus 0–20 uL MAb S25-23

| fraction number | +0 uL | +10 uL | +20 uL |
| --- | --- | --- | --- |
| 2 | 54.0 | 96.0 | 117.4 |
| 3 | 52.1 | 118.3 | 128.1 |
| 4 | 43.2 | 81.9 | 88.7 |
| 5 | 43.7 | 48.9 | 56.7 |
| 6 | 31.3 | 39.6 | 42.4 |
| 7 | 34.3 | 34.0 | — |
| 8 | 34.8 | 33.2 | — |
| 9 | 37.0 | 31.8 | — |

EXAMPLE 2

Preparation of Complex of Fluorescently Labeled Chlamydia Antigen and Antibody

A stock solution of the fluorescently labeled Chlamydia substrate of Example 1 was prepared in PBS (phosphate buffered saline) buffer at a concentration of 1 nM. Solutions of three antibodies were prepared with this stock solution and diluted serially 2:1 to give ten dilutions of each. The three antibodies were: (1) S25-23 a monoclonal antibody specific to the Chlamydia pentasaccharide carbohydrate antigen obtained from Dr. Helmut Brade of the Forschunginstitut Borstel, Borstel, Germany; (2) BDRC CT403, a second monoclonal with high affinity for the Chlamydia pentasaccharide antigen prepared by the inventor using techniques well known to those skilled in the art from Fu, Y. et al, *Infect. Immun.* 60: 1314 (1992); and (3) S23-24, a monoclonal antibody specific to the tetrasaccharide portion of the Chlamydia antigen (i.e., it is lacking the terminal 2–8 linked KDO sugar). This third monoclonal antibody was used as a negative control.

All experiments were done in duplicate with the Jolley FPM-I fluorometer Jolley Consulting and Research, Inc., Round Lake, Ill.), and both fluorescence polarization and total fluorescence intensity were obtained for each antibody concentration at room temperature following a 30 minute incubation time. The concentration range for each antibody was approximately 0.1 to 1000 nM.

The Jolley FPM-1 fluorometer had L-format polarized optics, and was equipped with a set of standard interference filters for fluorescein supplied by the manufacturer, a high intensity quartz-halogen light source, and photomultiplier tube detector. Experiments were run with the sample chamber at ambient temperature (typically 22° C.) and samples were introduced in 12×75 mm borosilicate glass tubes. Blank solutions containing only buffer were read and subtracted prior to data acquisition. Polarization (P) values are expressed in mP (1 mP=0.001 P) and are derived from measurements of polarized emission intensity parallel to (Ipa) and perpendicular (Ipe) to the plane of excitiation according to the following equation:

$$P = \frac{Ipa - Ipe}{Ipa + Ipe}$$

Figure 4:
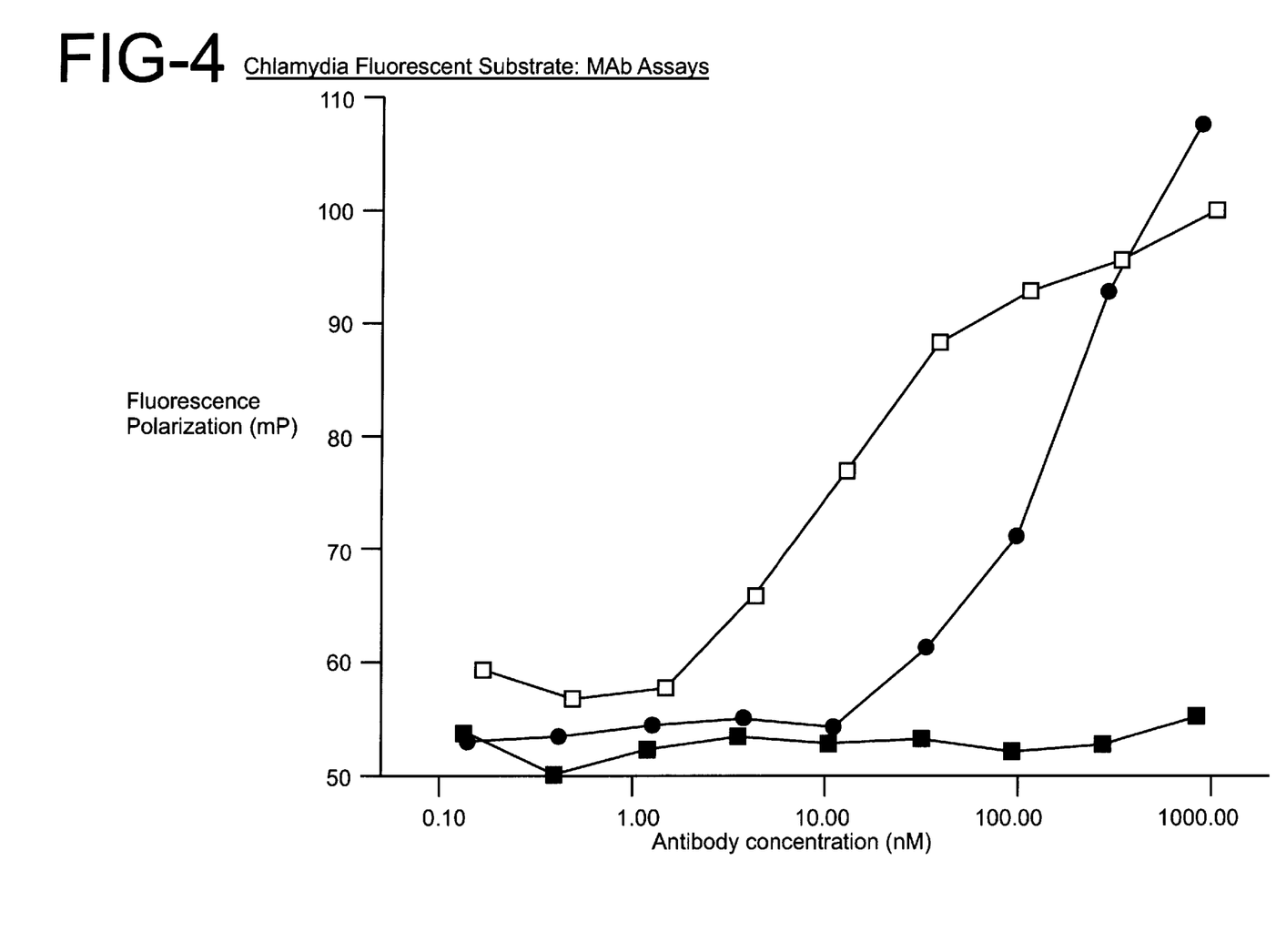
FIG. 4 is a graph showing titration of fluorescence polarization of fluorescently labeled Chlamydia antigen with different antibodies.

Results of these experiments are shown in FIG. 4. Briefly, the substrate from Example 1 bound with the highest apparent affinity to the CT403 antibody, and began to show a significant increase in fluorescence polarization with antibody concentrations greater than 1 nM. Apparent binding affinity to the S25-23 antibody was approximately ten-fold less than to CT403. No significant change occurred in fluorescence polarization upon titration with antibody S23-24, even at antibody concentrations near 1 uM. This last result is consistent with the poor binding of this antibody to the Chlamydia tri-KDO epitope as reported by Fu, Y. et al.

Because fluorescence polarization values and fluorescence anisotropy values are mathematically interconvertible, the above described assay method may be used with fluorescence anisotropy values as well. The mathematical relationship of polarization (P) and anisotropy (A) is expressed by the equation A=2P/(3-P).

EXAMPLE 3

Fluorescence Polarization Assay for Presence of Chlamydia Antigen in Sample

Fluorescence depolarization assay for Chlamydia lipopolysaccharide

A stock solution was prepared with the fluorescently labeled Chlamydia substrate from Example 1 (1 nM) and the antibody CT403 (20 nM) in both PBS buffer and in PBS buffer with 5% Triton-X-705 detergent (Sigma Chemicals, St. Louis Mo.). The Chlamydia lipopolysaccharide (LPS) (Dr. Helmut Brade, Forschunginstitut Borstel, Borstel, Germany) was mixed with these solutions in concentrations ranging from 0.51 to 30,000 ng/mL by serial dilution. The solutions were left for 60 minutes at room temperature in the dark before fluorescence measurements were taken.

Figure 5:
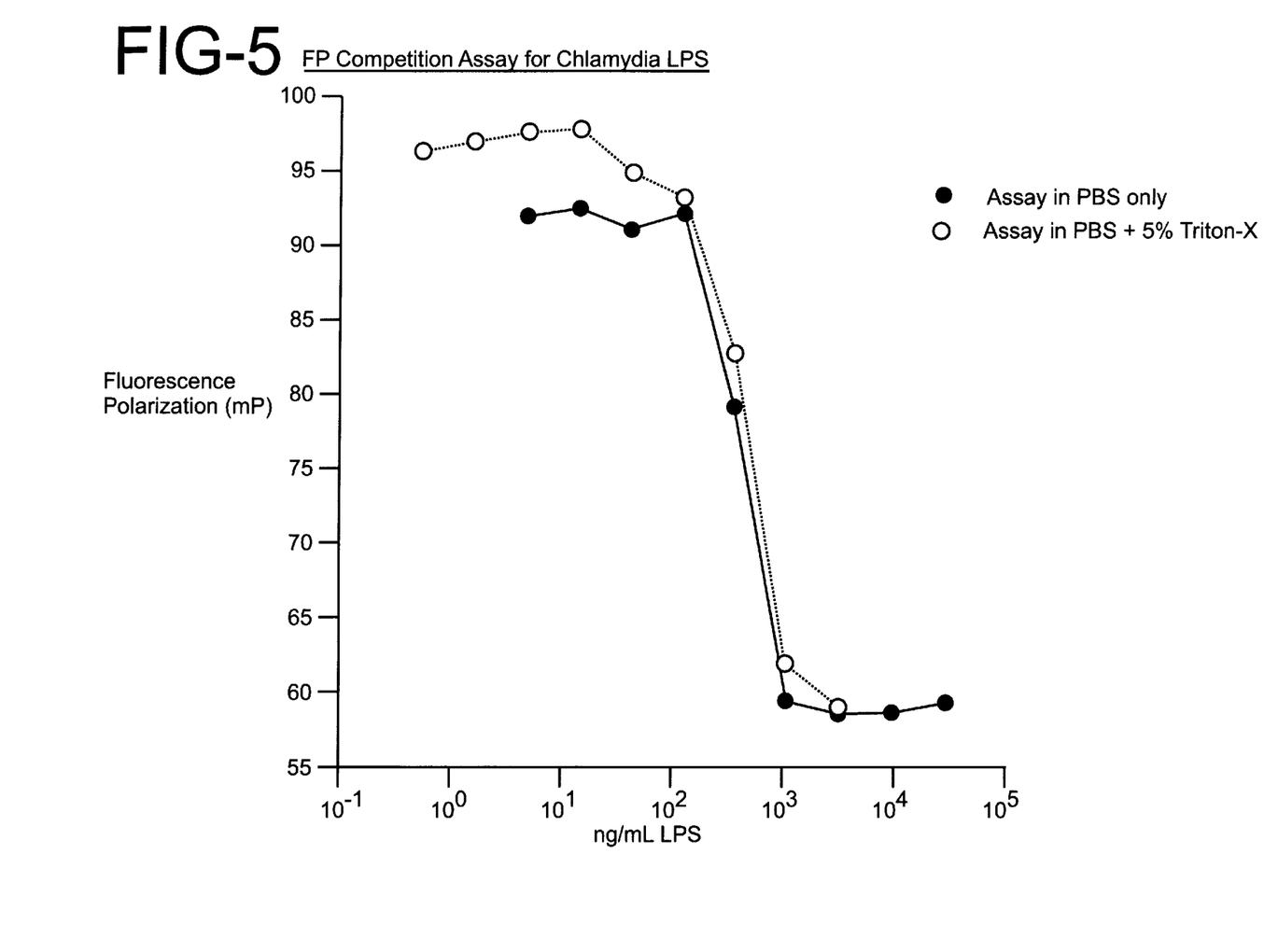
FIG. 5 is a graph showing the results of a fluorescence polarization immunoassay with Chlamydia lipopolysaccharide as the competitor with fluorescently labeled Chlamydia lipopolysaccharide antigen in the antibody/antigen complex.

Results of this experiment are shown in FIG. 5. Briefly, comparable binding to the substrate was found for the antibody CT403 in both PBS buffer and in PBS buffer with 5% Triton-X-705, an agent used to dissociate the Chlamydia LPS from intact Chlamydia organisms in clinical assays to render it accessible for immunoassay detection. Although the detergent appeared to have little effect on the direct binding of substrate to the antibody it was important to test this with the LPS antigen to determine if the intact lipid chains would impact the assay results. The detection limit appeared to be approximately 50–100 ng/mL in either buffer system. This is comparable to the sensitivity of other assay formats. The absolute sensitivity could be improved for clinical assay formats if it was performed in smaller volumes than 1 mL. For cervical swab specimens this would be an important advatage.

Due to the relationship of fluorescence polarization values and fluorescence anisotropy values, the results of the assay can be easily converted to fluorescence anisotropy.

Kinetic analysis of depolarization assay

Figure 6:
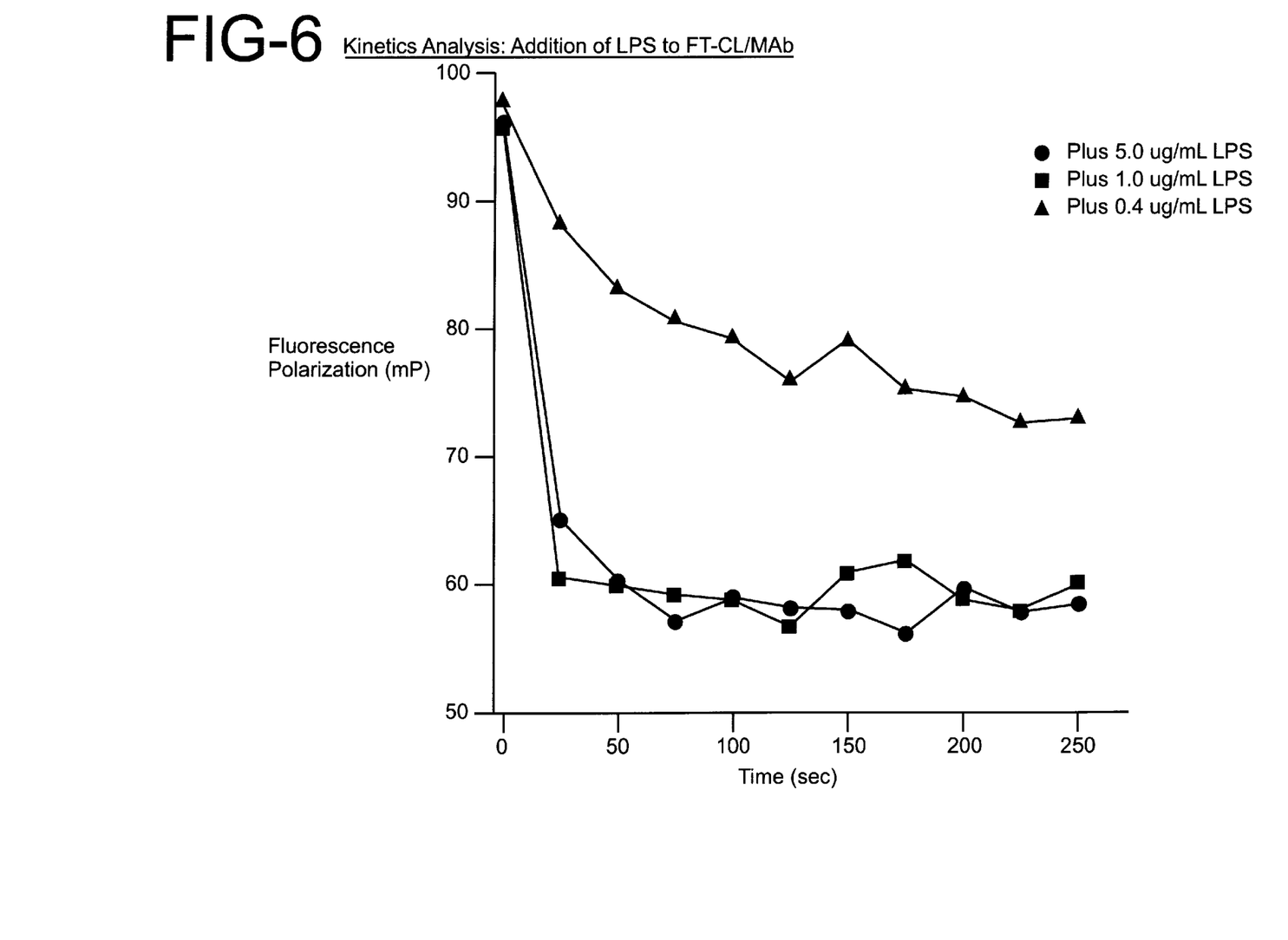
FIG. 6 is a graph showing the results of a kinetic analysis of the rate of the competitive immunoassay graphically depicted in FIG. 5.

A kinetic analysis of the above described depolarization assay was also performed with an analogous procedure comparing 0.4, 1.0, and 5.0 ug/mL LPS added to the substrate and CT403 antibody followed over a range of 0 to 250 seconds (FIG. 6). Briefly, even the lowest concentration (0.4 ug or 400 ng) produced a significant signal within two minutes. This demonstrates the feasibility of using the fluorescently labeled Chlamydia antigen of the present invention in rapid immunoassys which might be valuable in point of care testing (STD clinics, etc.).

EXAMPLE 4

Fluorescence Intensity Assay for Presence of Chlamydia Antigen in Sample The materials and procedures of Example 3 (Fluorescence depolarization assay for Chlamydia lipopolysaccharide) are used except that fluorescence intensity values are obtained rather than fluorescence polarization values. Similar results to Example 3 are expected. The number of organisms expected to be detectable by this method (approx. >$10^4$ org/mL) is comparable to manual immunoassays which use enzyme substrates for detection. With the instrument used for the fluorescence intensity measurements, the minimum volume is 1 mL. The detection limit in terms of the absolute number of organisms per sample could be improved by decreasing the volume required for the assays.

While the present invention has been described with some specificity, modifications apparent to those of ordinary skill in the art may be made without departing from the scope of the invention. Various features of the invention are set forth in the following claims.

That which is claimed is:

1. A compound of the formula:

$R$ =—OH or —$OPO_3H_2$ and

2. A compound of the formula:

R=—OH or —OPO$_3$H$_2$.

3. A composition comprising the compound of claim 1 and the compound of the formula:

R=—OH or —OPO$_3$H$_2$.

* * * * *